(12) United States Patent
Tao et al.

(10) Patent No.: US 10,744,286 B2
(45) Date of Patent: Aug. 18, 2020

(54) DEVICES AND METHODS FOR SURGICAL FIRE PREVENTION

(71) Applicants: Jeremiah P. Tao, Newport Coast, CA (US); Thomas M. Tao, Greer, SC (US)

(72) Inventors: Jeremiah P. Tao, Newport Coast, CA (US); Thomas M. Tao, Greer, SC (US)

(*) Notice: Subject to any disclaimer, the term of this patent is extended or adjusted under 35 U.S.C. 154(b) by 662 days.

(21) Appl. No.: 14/295,533

(22) Filed: Jun. 4, 2014

(65) Prior Publication Data
US 2014/0366890 A1    Dec. 18, 2014

Related U.S. Application Data

(60) Provisional application No. 61/843,818, filed on Jul. 8, 2013, provisional application No. 61/836,023, filed on Jun. 17, 2013.

(51) Int. Cl.
*A61M 16/00* (2006.01)
*A61B 46/00* (2016.01)
*A61M 16/06* (2006.01)

(52) U.S. Cl.
CPC ........... *A61M 16/009* (2013.01); *A61B 46/00* (2016.02); *A61B 46/40* (2016.02); *A61M 16/06* (2013.01); *A61M 2202/02* (2013.01)

(58) Field of Classification Search
CPC ......... A61M 16/06–08; A61M 16/0087–0093; A61M 16/009; A61M 16/0841–0858; A61M 16/0883; A61M 16/0891; A61M 16/10–1005; A61M 16/104; A61M 16/18; A61M 2016/102–1035; A62B 7/00–14; A62B 18/00–06; A62B 23/00–025; A41D 13/11–12; A41D 13/1107;
(Continued)

(56) References Cited

U.S. PATENT DOCUMENTS 4,015,598 A * 4/1977 Brown ................ A61M 16/009
128/205.25
4,041,203 A    8/1977 Brock et al.
(Continued)

FOREIGN PATENT DOCUMENTS

JP    2010284385    12/2010
WO    WO 1999/13793    3/1999
WO    WO 2012/103490    8/2012

OTHER PUBLICATIONS

Reyes et al., Supplement Oxygen: Ensure Its Safe Delivery During Facial Surgery,95:924-8, 1995.
(Continued)

*Primary Examiner* — Keri J Nelson
*Assistant Examiner* — Michelle J Lee
(74) *Attorney, Agent, or Firm* — Charlotte C. Wilson

(57) ABSTRACT

Surgical devices and methods described herein reduce the risk of surgical fires for patients receiving supplemental oxygen. Airflow with elevated concentrations of oxygen is drawn away from a surgical field when the tubing is fluidly connected to a suction source. Tubing may be strategically positioned at locations presenting risk of oxygen gas buildup, such as the nasofacial sulcus or bucco-facial sulcus. Apertures are present in the turbine wall to draw airflow away from the surgical field and into the tubing. Various embodiments are contemplated in which the tubing is used with a surgical mask or a surgical drape, and a method of use is provided.

4 Claims, 7 Drawing Sheets

(58) Field of Classification Search
CPC ............ A41D 13/1138; A41D 13/1146; A61B 46/00–20; A61B 46/23; A61B 46/40; A61B 2046/205; A61B 2046/234–236
See application file for complete search history.

(56) References Cited

U.S. PATENT DOCUMENTS

| | | | |
|---|---|---|---|
| 4,589,408 A | | 5/1986 | Singer |
| 4,739,753 A | | 4/1988 | Brehm |
| 4,770,169 A | * | 9/1988 | Schmoegner ......... A61M 16/06 128/206.24 |
| 5,140,997 A | | 8/1992 | Glassman |
| 5,145,727 A | | 9/1992 | Potts et al. |
| 5,156,618 A | * | 10/1992 | Fiore et al. ....... A61M 16/0054 128/206.11 |
| 5,169,706 A | | 12/1992 | Collier, IV et al. |
| 5,443,606 A | | 8/1995 | Hassenboehler, Jr. et al. |
| 5,474,060 A | | 12/1995 | Evans |
| 6,237,596 B1 | | 5/2001 | Bohmfalk |
| 6,298,855 B1 | | 10/2001 | Baird |
| 6,843,252 B2 | | 1/2005 | Harrison et al. |
| 7,243,649 B2 | * | 7/2007 | Moenning ............. A61M 16/06 128/203.12 |
| 2003/0024533 A1 | | 2/2003 | Sniadach |
| 2004/0000313 A1 | | 1/2004 | Gaynor |
| 2005/0005943 A1 | | 1/2005 | Lanier |
| 2005/0257791 A1 | | 11/2005 | Biederman |
| 2006/0174886 A1 | * | 8/2006 | Curti ................ A61M 16/0054 128/206.11 |
| 2012/0271187 A1 | * | 10/2012 | McNeill ............... A61M 16/04 600/532 |

OTHER PUBLICATIONS

Fire Safety in the Operating Room, Rinder CS, Curr Opin Anaesthesiol 21:790-5, 2008.
Electrosurgical Burn Injuries and Their Prevention Battig CG, J.A.M.A. 204:1025, 1968.
Daane et al., Fire in the Operating Room: Principles and Prevention, 115:73e-5e, 2005.
Nonwoven Facemesks for Healthcare Applications, Johnson, RA. Technical Textile Trade Journal, p. 32-35. Mar. 2003.
The Efficacy of a Midfacial Seal Drape in Reducing Oculofacial Surgical Filed Fire Risk, Tao et al, ASOPRS Fall Symposium, Orlando, FL. Oct. 2011.
Nonwovens in Medical Textiles, Lickfield DK, International Fiber Journal, p. 42-48, Aug. 2001.
Fire Prevention During Surgery, Magruder et al., Arch. Opthhalmol. 84:237, 1970.
Operating Room Fires, part II, Optimizing Safety, Engel et al., Plast. Reconstr. Surg. 130:681-9, 2012.
Recommended Practices: Protective Barrier Materials for Surgical Gowns and drapes, Assoc. of Oper. Room Nurses (AORN), Journal 55(2): 832-835, 1992.
Liquid Smiler Properties of Nine Surgical Gown Fabrics, McCullough et al. INDA Journal 3(3): 14-20, 1991.
Principles and Hazards of Electrocautery in Otolaryngology, Bell et al, Otolaryngol. Head Neck Surg. 94:504, 1986.
Accidental Burns Associated with Electrocautery, Wald et al. J.A. M.A. 217:916, 1971.
An unusual Complication Associated with Blepharoplasty, Aston et al, Aesthetic Plast. Surg. 2:451, 1978.
Thomas, Shane. PCT Notification of Transmittal of the International Search Report and the Written Opinion of the International Searching Authority or the Declaration, dated Nov. 7, 2014, pp. 1-10.

* cited by examiner

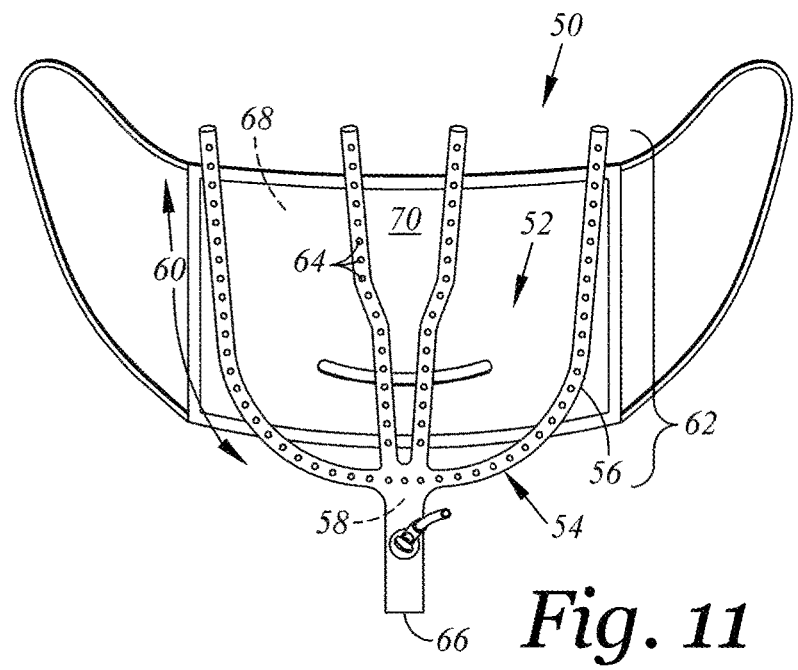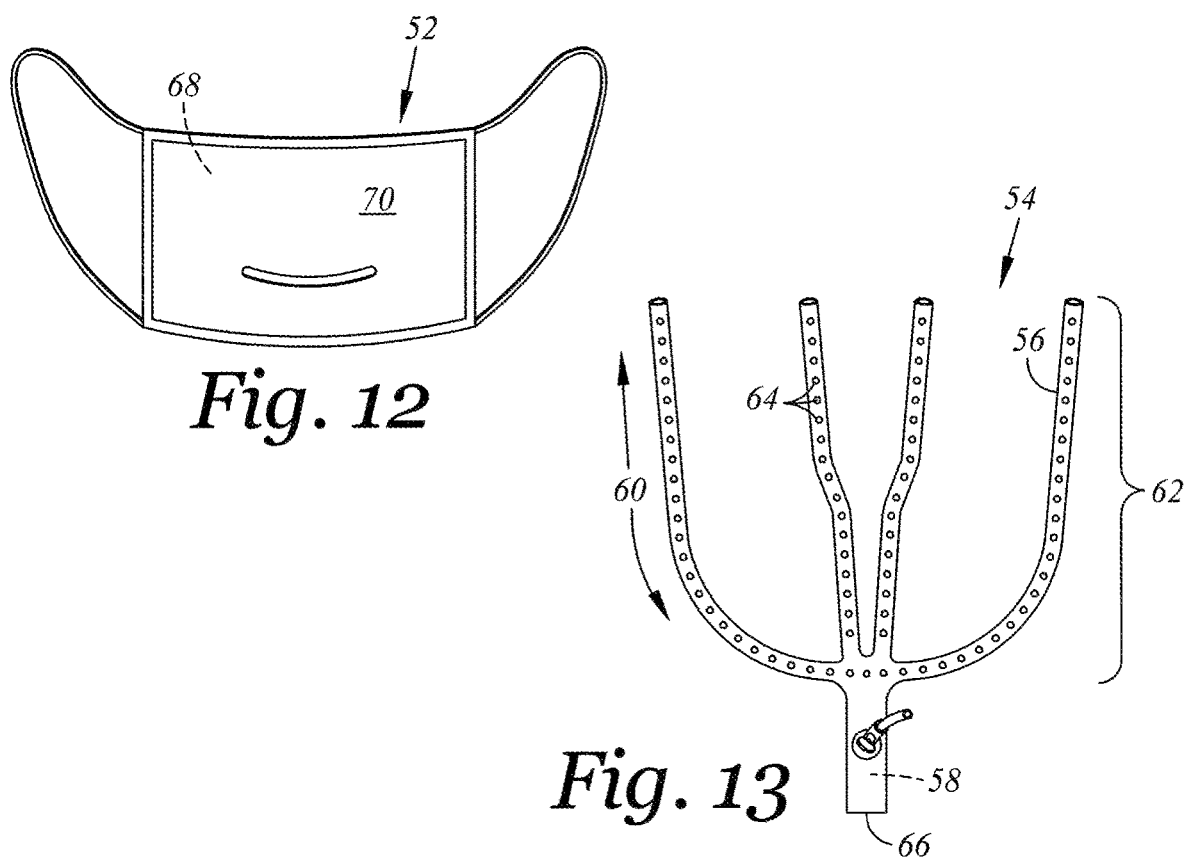

DEVICES AND METHODS FOR SURGICAL FIRE PREVENTION

CROSS-REFERENCE TO RELATED APPLICATIONS

The present application relates to and claims the benefit of U.S. Provisional Application No. 61/836,023, filed Jun. 17, 2013 and entitled "A MIDFACIAL DRAPE FOR SURGICAL FIRE PREVENTION," and to U.S. Provisional Application No. 61/843,818, filed Jul. 8, 2013 and entitled "A MIDFACIAL DRAPE FOR SURGICAL FIRE PREVENTION," all of which are wholly incorporated by reference herein.

STATEMENT RE: FEDERALLY SPONSORED RESEARCH/DEVELOPMENT

Not applicable

BACKGROUND

1. Technical Field

The present disclosure relates generally to surgical masks and drapes, and more particularly to protective surgical masks and drapes that can forestall a flash fire accident during facial and head operations during which electrosurgical or laser devices and supplemental oxygen are in close proximity.

2. Related Art

Operating-room fires are associated with significant morbidity and even mortality. Despite awareness and other preventative tactics, many operating room fires are reported each year. The medical literature is replete with articles highlighting the risks. Face and head surgeries are, more often than ever, being performed with electrosurgical or laser devices in combination with nasal cannulated oxygen, making the prospect of fire a serious and growing concern. Although drastically underreported, the Emergency Care Research Institute estimated that between 200 and 240 surgical fires occurred in the United States in 2012, making the frequency of their occurrences comparable to that of other surgical mishaps, such as wrong-side surgery or retained instruments.

For surgical fires to occur, three environmental conditions must be present simultaneously: an oxidizer (eg: oxygen, nitrous oxide), an ignition source (eg: electrocautery, electrosurgical devices, lasers), and a fuel (eg: alcohol-based prepping agents, aerosols, oily substances, hair, surgical gowns, drapes, towels, hoods, masks, tissues). During many surgeries, especially those performed with the patient under conscious sedation, patients are routinely provided with a supplemental oxygen supply via a nasal cannula or a mask. Of reported hospital fires, nearly three quarters have been identified as having an oxygen-rich atmosphere as a significant contributing factor. Further, the threshold for combustion of materials that may not normally be expected to combust in ambient air may be breached with oxygen flow rates as low as 2 liters per minute. Oxygen supplementation is commonly given at 2 to 6 liters/min. An enriched oxygen environment increases the flammability risk of human tissues as well as drapes, cleansing solutions, and other materials common in the operating room. Oxygen tubing itself may even ignite and can create a dangerous blowtorch effect if the oxygen is still flowing.

One general tactic for preventing surgical fires during the use of supplemental oxygen and an electrosurgical or laser devices which could function as an ignition source is to cut off the flow of supplemental oxygen at least one minute before the use of those devices, to allow lingering pockets of air with elevated oxygen concentration to dissipate, and to not restart the flow of supplemental oxygen until the electrosurgical or laser device is no longer being used.

However, this tactic is not always flawless, as the continued and growing prevalence of surgical fires shows. For example, the delivery of supplemental oxygen during a surgery performed under conscious sedation will usually fall under the supervision of an anesthesiologist, while the electrosurgical or laser device will be used by a surgeon, both of whom are very focused on their own individual tasks. This presents a situation where miscommunication between the surgeon and the anesthesiologist may result in a failure to cut off the supplemental oxygen supply at least a minute prior to use of the electrosurgical or laser device, or at all. This risk may be further exacerbated in surgical settings where these devices may be used frequently and often in response to rapidly changing patient conditions, such as abrupt bleeding. Additionally, in patients with poor cardiopulmonary function, discontinuing the supplemental oxygen supply at any point may be highly undesirable.

Other tactics for preventing surgical fires face similar challenges. For example, extending the nasal cannula prongs with nasopharyngeal tubing may mitigate some risk due to the supplemental oxygen being delivered deeper into the patient's respiratory tract. However, this tactic is likewise limited, because it may result in sub-optimal oxygen delivery due to additional patient discomfort and impaired nasal air exchange. Further, during surgeries directly performed on a patient's upper respiratory tract, this may further heighten the risk of surgical fire, as the supplemental oxygen may become even more concentrated in the upper respiratory tract, and the nasopharyngeal tubing may, in areas of high oxygen concentration, be set aflame.

In view of a foregoing, there is a need in the art for a surgical mask for surgical fire prevention.

BRIEF SUMMARY

In accordance with embodiments of the present disclosure, there are provided surgical masks that may mitigate combustion during surgical operations and possibly self-extinguish a fire if and when it may occur. Typically, a significant hazard for fire exists at a 26% or greater oxygen concentration. Oxygen, being heavier than ambient air, may naturally pool in the crevices of a patient's face when delivered by nasal cannula, and may inadvertently approach or exceed this threshold. Therefore, according to some embodiments of the present disclosure, the masks may be used to prevent such a dangerous pooling of oxygen, and to contain and evacuate oxygen that may leak out and collect at a patient's face during the delivery of supplemental oxygen.

In one particular embodiment, a surgical mask connectable to a suction source for reducing the risk of surgical fire near a surgical patient's face during the use of supplemental oxygen is envisioned to comprise a surgical drape having a patient side and a surgeon side, with the surgical drape being sized and configured for placement adjacent a surgical patient's face. An elongated tubing is attached to the surgical drape, with a tubing wall defining a tubing length and with the tubing wall having an aperture portion along the tubing length, with the aperture portion being attached to and coplanar with the surgical drape. A port is included which is sized and configured to be disposed in fluid communication with a suction source. A lumen is formed within the tubing wall, and the lumen is disposed in fluid communication with the port. A plurality of apertures is formed in and disposed along the aperture portion of the tubing wall, and are disposed in fluid communication with the lumen. The apertures are sized and configured to be positionable proximal to the surgical patient's face, and to allow airflow to be drawn away from the surgical patient's face and through one or more of the plurality of apertures, through the lumen, and through the port while the port is placed in fluid communication with the suction source. It is contemplated that the surgical drape may be sized and configured for placement adjacent a surgical patient's nose, or adjacent a surgical patient's nose and mouth.

In variations of the above embodiment, the tubing may be integrated with the surgical drape, and the tubing wall may even be formed to be contiguous with the surgical drape. The plurality of apertures may be positioned on the patient side of the surgical drape, on the surgeon side of the surgical drape, or on both the patient side and the surgeon side of the surgical drape.

A portion of the aperture portion may be configured to align with a surgical patient's nasofacial sulcus or a patient's bucco-facial sulcus when the surgical drape is placed adjacent a surgical patient's face. In a particular embodiment, a first portion and a second portion of the aperture portion of the tubing are configured to align with each of a surgical patient's respective nasofacial sulcus, and a third portion and a fourth portion of the aperture portion are configured to align with each of a surgical patient's respective buccofacial sulcus. In some embodiments, the tubing may be formed in a branched configuration.

The surgical drape may comprise a polymer. The surgical drape may also comprise a laminate of a melt-blown layer and a spun-bond layer. In certain embodiments, the surgical drape may comprise a fire retardancy or anti-static additive.

In another particular embodiment, a surgical mask for placement adjacent a surgical patient's face and connectable to a suction source for reducing the risk of surgical fire near a surgical patient's face during the use of supplemental oxygen in contemplated, with the surgical mask comprising a housing for placement adjacent a surgical patient's face, and a first tubing. The housing has an outer perimeter sized and configured to contour along a surgical patient's face with the surgical mask placed adjacent a surgical patient's face. The first tubing comprises a first tubing wall defining a first tubing length, with the first tubing length having a first aperture portion along the first tubing length, and with the first aperture portion being attached adjacent the outer perimeter of the housing. The first tubing has a port sized and configured to be disposed in fluid communication with a suction source, a first lumen being formed within the first tubing wall and disposed in fluid communication with the first port, and a plurality of first apertures formed in and disposed along the first aperture portion and disposed in fluid communication with the first lumen. The first apertures are sized and configured to be positionable proximal the surgical patient's face, causing airflow to be drawn away from the surgical patient's face and through one or more of the first apertures, through the first lumen, and through the port while the port is placed in fluid communication with the suction source. In particular embodiments, the surgical mask is a nasal mask configured for placement adjacent a surgical patient's nose, or is an oronasal mask configured for placement adjacent a surgical patient's nose and mouth.

In variation of this embodiment, the housing may further comprise an inner perimeter defining an opening through the housing, the opening being sized and positioned so as to generally align with a surgical patient's mouth with the housing placed adjacent a surgical patient's face. The inner perimeter of the housing is also sized and configured to contour along a surgical patient's face with the housing is placed adjacent a surgical patient's face. A second tubing is positioned at the inner perimeter of the housing, with the second tubing comprising a second tubing wall defining a second tubing length, the second tubing length having a second aperture portion along the second tubing length. The second aperture portion is adjacently attached to the inner perimeter of the housing. A second lumen is formed within the second tubing wall, with the second lumen being disposed in fluid communication with the port. A plurality of second apertures are formed in and disposed along the second aperture portion and are disposed in fluid communication with the second lumen. The second apertures are sized and configured to be positionable proximal to the surgical patient's face so as to allow airflow to be drawn away from the surgical patient's face and through one or more of the second apertures, through the second lumen, and through the port when the port is placed in fluid communication with the suction source.

In further embodiments of this variation, the outer perimeter of the housing may surround the inner perimeter of the housing, or the outer perimeter of the housing and the inner perimeter of the housing may be at least partially coextensive. The first lumen may also be disposed in fluid communication with the second lumen. It is further contemplated that the surgical mask may further comprise a cannula for delivering supplemental oxygen attached to the housing.

A method for reducing the risk of surgical fire at a surgical site with a suction source during the use of supplemental oxygen is additionally contemplated. The first step of the method comprising positioning an elongated tubing proximal to a surgical site. The tubing comprises a tubing wall defining a tubing length, with the tubing wall having an aperture portion along the tubing length, a port sized and configured to be disposed in fluid communication with a suction source, a lumen formed within the tubing wall, the lumen disposed in fluid communication with the port, and a plurality of apertures formed in and disposed along the aperture portion and disposed in fluid communication with the lumen. The apertures are sized and configured to be positionable proximal the surgical patient's face, such that airflow is drawn away from the surgical site and through one or more of the plurality of apertures, through the lumen, and through the port when the port is placed in fluid communication with the suction source. The second step of the method is to place the port in fluid communication with the suction source.

BRIEF DESCRIPTION OF THE DRAWINGS

These and other features and advantages of the various embodiments disclosed herein will be better understood with respect to the following description and drawings, in which:

FIG. 11 is a front view of a surgical mask for reducing the risk of surgical fire according to one embodiment;

FIG. 12 is a front view of the surgical drape of the embodiment of FIG. 11;

FIG. 13 is a front view of the elongated tubing of the embodiment of FIG. 11;

Common reference numerals are used throughout the drawings and the detailed description to indicate the same elements.

DETAILED DESCRIPTION

According to various aspects of the present invention, an improved surgical mask for preventing surgical fires during the use of cannulated oxygen is contemplated, which utilizes tubing that may be placed in fluid communication with a suction source to draw airflow away from a surgical patient containing elevated levels of oxygen. It is contemplated that the tubing may include a tubing wall with a plurality of apertures disposed along an aperture portion of the tubing wall, the tubing wall forming a lumen which may be fluidly connected to a suction source via a port. One particular embodiment utilizes a surgical mask configuration in which the aperture portion of the tubing is attached adjacent the outer perimeter of the housing of the surgical mask. Another variant of the surgical mask embodiment further includes an opening through the housing positioned to align with a surgical patient's mouth to permit speech by the patient or access to the mouth by the surgeon, and further includes similar tubing along the inner perimeter of the housing that defines the opening. A surgical drape embodiment is additionally contemplated in which the tubing is attached to a surgical drape, and, in more particular embodiments, is specifically designed to draw airflow away from a patient's nasofacial sulcus and bucco-facial sulcus. A further variant of the surgical drape embodiment integrates the tubing with the surgical drape itself.

Figure 1:
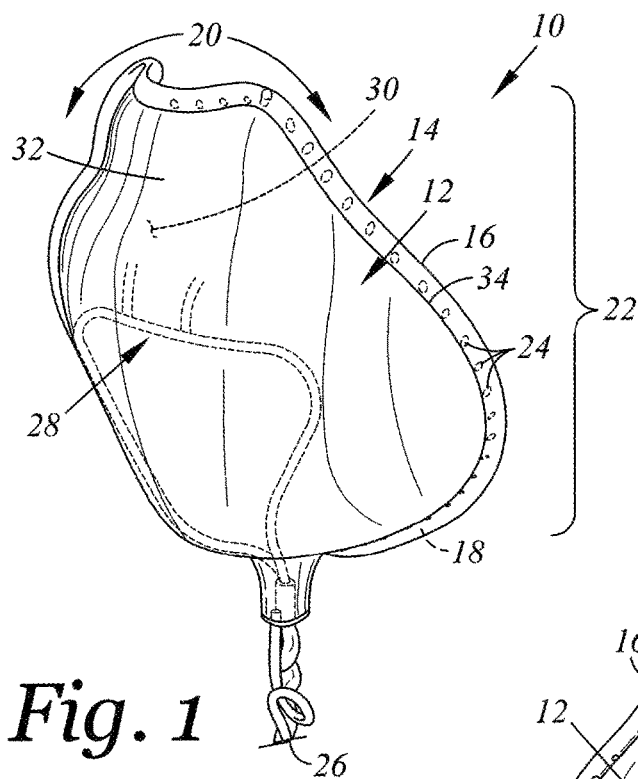
FIG. 1 is a perspective view of a surgical mask for reducing the risk of surgical fire according to one embodiment.

Referring now to the drawings, and more particularly to FIG. 1, a surgical mask device 10 according to an exemplary embodiment is shown. In such an exemplary embodiment, the surgical mask device 10 may include a housing 12, a first tubing 14, a first tubing wall 16, a first lumen 18, a first tubing length 20, a first aperture portion 22, a plurality of first apertures 24, a tubing port 26, and a cannula 28.

The housing 12 may be formed of may be formed of one or more materials usable in the making of medical devices, including, for example but without limitation, plastics, polymers, metals, or ceramics. Preferably, the housing 12 is formed of a dense, resilient, moderately flexible material. More preferably, the housing 12 is formed of a transparent or translucent polymer. In the exemplary embodiment, the housing 12 has a housing patient side 30 and an opposing housing surgeon side 32. The housing patient side 30 may be generally concave so as to fit over the nose and mouth of a surgical patient, and the housing surgeon side 32 may be generally convex. The housing 14 may have at its edge or edges an outer perimeter 34 sized and configured to contour along a surgical patient's face. An outer perimeter 34 is sized and configured to contour along a surgical patient's face when that outer perimeter 34 is formed such that when the housing 12 is placed and aligned adjacent a surgical patient's face, the form of the housing 12 is such that when aligned the outer perimeter 34 approaches the typical surgical patient's face. While surgical patients may have varying lower facial features, it is an object of the design of the housing 12 that it may be usable for its intended purpose with as many surgical patients as possible, and as such while not all points along the outer perimeter 34 must align perfectly with the contours of every surgical patient's face, it may be preferred that the housing 12 be formed such that most surgical patients will be able to have it placed over their nose and/or nose and mouth comfortably, with points along the outer perimeter 34 being the portion of the housing 12 which most closely approaches their face when the housing 12 is correctly aligned. As such, it may be preferable that the housing 12 be bilaterally symmetrical to match the typical surgical patient's face, and may in certain embodiments have an arcuate horizontal cross-section. Being configured for placement adjacent a surgical patient's face means that the housing 12 is configured to be able to be placed generally proximal to one or more areas of a surgical patient's face, including but not limited to the surgical patient's nose, or the surgical patient's nose and mouth.

The first tubing 14 may be formed of one or more materials usable in the making of medical tubing, including but not limited to plastics, polymers, or rubbers. Preferably, the first tubing 14 is formed of a smooth, flexible material that does not cause significant discomfort when contacted with a surgical patient's face, though is also stiff enough to maintain its structural integrity and not kink or block flow of air when lightly compressed by the housing 12 being placed against a surgical patient's face. In a preferred embodiment, the first tubing 14 is formed of latex, rubber, or polyvinyl chloride. However, it may be seen that any material may be utilized to form the first tubing 14 so long as that material is suitable for the intended purpose of evacuating oxygen-rich air away from a surgical patient. In the exemplary embodiment, the first tubing 14 is formed to be looped unbroken around the outer perimeter 34 of the housing 12. Alternately, in other embodiments, the first tubing 14 may have breaks, branches, and terminations. The first tubing 14 may have a first tubing wall 16, a first lumen 18, a first tubing length 20, a first aperture portion 22, and a plurality of first apertures 24.

The first tubing wall 16 may at least partially define the exterior of the first tubing 14, and may at least partially circumscribe and define the first lumen 18. The first tubing wall 16 preferably when not deformed has a generally circular cross-section, but is contemplated herein that the first tubing wall 16 may also have a differently shaped cross-section. The first tubing wall 16 preferably has a constant geometric cross section, cross-section area, and thickness throughout the first tubing length 20, but in other embodiments the first tubing wall 16 may vary in geometric cross-section, cross-sectional area, and thickness throughout the first tubing length 20. For example, in certain embodiments it may be beneficial to utilize a first tubing wall 20 having a larger geometric cross-section, so as to better fit the face of a smaller patient and result in a more effective seal to prevent the leakage of oxygen-rich air. In other embodiments, it may be beneficial to configure the first tubing wall 16 to be more pliant and deformable at the first aperture portion 22, thereby providing a greater degree of conformity to the patient, and to be more resilient at other areas, thereby preventing kinking or occlusion which may result in ineffectiveness of the device.

The first lumen 18 may be formed within the first tubing wall 16, and may be fluidly connected to the first apertures 24 and the tubing port 26. The first lumen 18 may provide a pathway for oxygen-rich airflow to travel through so that the airflow is removed from the surgical site where it may present an elevated risk of surgical fire in the presence of electrosurgical instruments or lasers. Being formed within the first tubing wall 16, the first lumen 18 likewise has a cross-section and cross-sectional area defined by the interior of the first tubing wall 16, which in a preferred embodiment is generally circular, though in other embodiments, may take other forms, such as elliptical, oval, rectangular, square, or otherwise.

The first tubing length 20 may be the length defined by the first tubing wall 16. In the exemplary embodiment, the first tubing 16 has a first tubing length 20 that is roughly equivalent to the outer perimeter 34 of the housing 12 plus the distance from the outer perimeter 34 to the tubing port 26. In other embodiments, different configurations of the housing 12, the first tubing 14, and the tubing port 26 may result in a different first tubing length 20.

The first aperture portion 22 may be the portion of the first tubing length 20 of the first tubing wall 16 that has the plurality of first apertures 24 formed in and disposed along the first tubing wall 16. In the exemplary embodiment, the first aperture portion 22 is the portion of the first tubing length 20 which is attached adjacent to the outer perimeter 34 of the housing 12. Alternately, in other embodiments, the first aperture portion 22 may be configured differently so as to attach to the housing at different areas. For example, the first aperture portion 22 may be attached at only a portion of the outer perimeter 34 of the housing 12, may be staggered or broken up to be at multiple locations along the outer perimeter 34 of the housing 12, or may be oriented and configured in other configurations. The first aperture portion 22 may be attached adjacent the outer perimeter 34 of the housing 12. In the exemplary embodiment, the first aperture portion 22 is adjacent to substantially the entire length of the outer perimeter 34, and is attached to the outer perimeter 34 so as to create an airtight seal between the material of the first tubing wall 16 and the outer perimeter 34. Alternately, in other embodiments, the first aperture portion 22 may not be adjacent to substantially the entire length of the outer perimeter 34, but instead may only be attached to a portion of the length of the outer perimeter 34, and the attachment between the first tubing wall 16 and the outer perimeter 34 may not be airtight. Such attachment may be achieved by, for example but without limitation, adhesives, fittings, fastenings, mountings, or any other ways of attaching components in medical devices together.

The plurality of first apertures 24 may be formed in and disposed along the first aperture portion 22 and be disposed in fluid communication with the first lumen 18. The first apertures 24 may also be sized and configured to be positioned proximal to the surgical patient's face to allow airflow to be drawn through the first apertures 24 and away from the surgical patient's face. The first apertures 24 may be, in the exemplary embodiment, small circular holes in the first tubing wall 20 which are closely spaced together. Alternately, the first apertures 24 may be configured in other ways and to have other forms, and may be, for example but without limitation, square, oval, rectangular, elliptical, or otherwise, may be spaced closer together or further apart, and may be arranged differently. In the exemplary embodiment, the first apertures 24 are positioned such that airflow is drawn through the first apertures 24 from both the housing patient side 30 and the housing surgeon side 32 of the housing 12 when the surgical mask device 10 is placed adjacent a surgical patient's face and connected to a suction source. However, in other embodiments, the first apertures 24 may be positioned to cause airflow to be drawn in from only the housing patient side 30, or only the housing surgeon side 32 of the housing 12, or to allow selectivity in the regions from which airflow will be drawn in.

The tubing port 26 may be any port that is in fluid connection with the first lumen 18 and that allows fluid connection to a suction source and the passage therethrough of airflow. The tubing port 26 may engage with an external suction source in any way which produces a sufficient seal to result in suction at the first apertures 24 to result in evacuation of airflow. Such engagement may be, for example but without limitation, threaded, frictional, or coupling engagement. In the exemplary embodiment, the tubing port 26 is the terminal end of the first tubing 14 which may fit over or be placed within a frictionally engaging seal, such as a nozzle head or a larger tube which may be secured with a tube or hose clamp. Alternately, in other embodiments, the tubing port 26 may be more elaborate, and may be, for example, a locking system configured to allow for more specific fluid connection to a particular suction source. In other embodiments, the port may also be used to transmit supplemental oxygen to the cannula 28, which may have the benefit of reducing the multiplicity of tubing connected to the housing 12. The tubing port 26 may also have control elements for initiating or regulating the flow therethrough of evacuated airflow, for controlling the suction power of the suction source remotely, or other control elements for modulating functionality of the surgical mask device 10.

The cannula 28 may be, in the exemplary embodiment, a nasal cannula for delivery of supplemental oxygen to the nares of a surgical patient. Alternately, the cannula 28 may be other forms of cannula or means of oxygen supplementation for a patient. For example, in certain embodiments, the cannula 28 may be open tubing which functions to elevate oxygen concentration in the ambient air on the housing patient side 30 of the housing 12 when the housing 12 is placed over a surgical patient and supplemental oxygen or other ventilation gas flows through the cannula 28. In other embodiments, the cannula 28 may be configured to deliver supplemental oxygen to deeper areas in the patient's respiratory tract. It has been recognized that placement of the cannula 28 on the patient side of the housing 12 and integration of the path of the cannula 28 through the housing 12 may allow the advantage of preventing a multiplicity of tubing in the surgical environment. The typical behind-the-ears nasal cannula may present a greater level of inconvenience or risk as compared to a nasal cannula integrated with or passing through the housing 12, since a typical behind-the-ears nasal cannula may result in a diminishment in the integrity of the seal of the first tubing 14 with the surgical patient's face.

Figure 2:
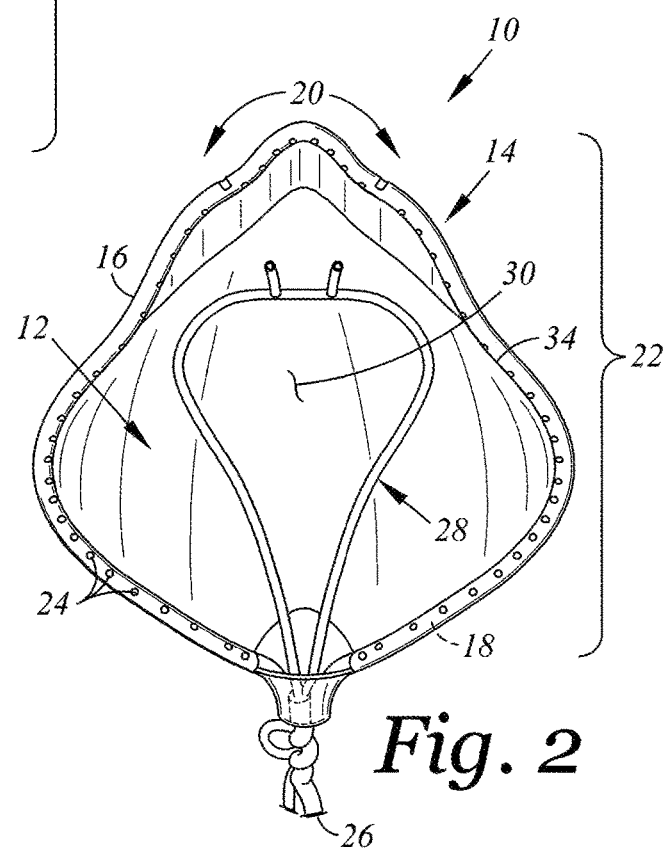
FIG. 2 is a rear view of the embodiment of FIG. 1.

Referring now to FIG. 2, a rear view from the housing patient side 30 of the exemplary embodiment of the surgical mask device 10 may be seen. It may be seen in particular that in the exemplary embodiment, at least some of the plurality of first apertures 24 are positioned so as to evacuate air from the patient side 30.

Figure 3:
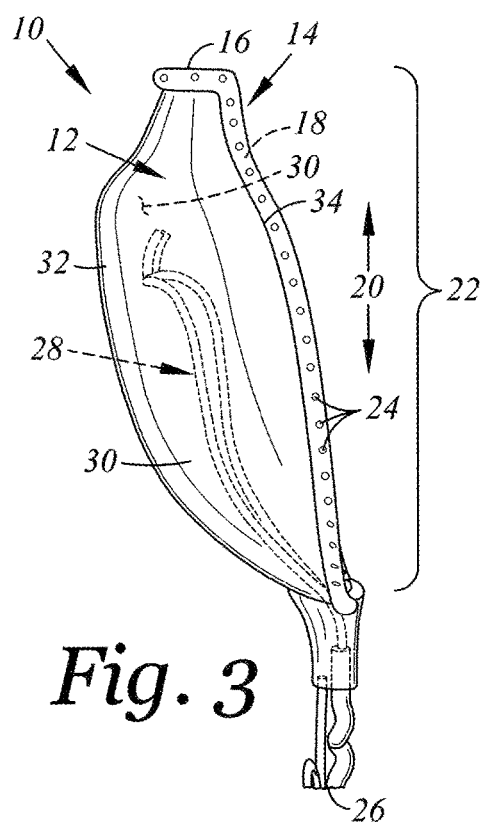
FIG. 3 is a side view of the embodiment of FIG. 1.

Referring now to FIG. 3, a side view of the exemplary embodiment of the surgical mask device 10 may be seen.

Figure 4:
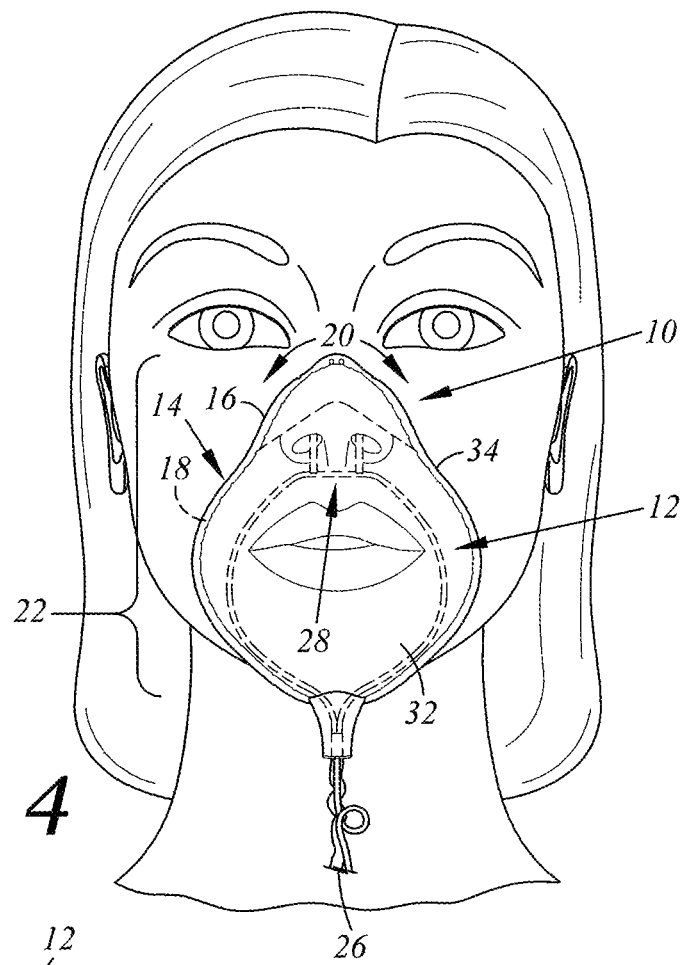
FIG. 4 is a front view of the embodiment of FIG. 1, showing placement adjacent a surgical patient's face.

Referring now to FIG. 4, a front view of the exemplary embodiment of the surgical mask device 10 may be seen placed adjacent a surgical patient's face. It may be seen that the cannula 28 may interface with the patient's nares. Elevated oxygen concentrations resulting from leakage of supplemental oxygen from a surgical patient's nose and mouth may be contained by the surgical mask device 10 due to the seal between the housing 12 and the surgical patient's face. As a result of the elevated oxygen concentrations being drawn into the apertures 24 and subsequently through the port 26, areas of elevated oxygen concentration may not be formed at those areas on the surgical patient outside of the housing 12.

Figure 5:
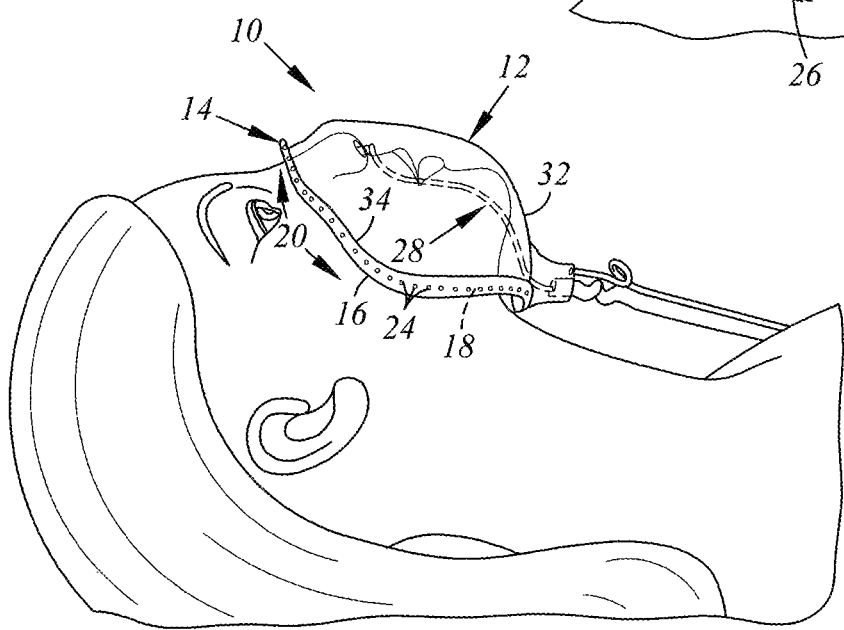
FIG. 5 is a side view of the embodiment of FIG. 1, showing placement adjacent a surgical patient's face.

Referring now to FIG. 5, a side view of the exemplary embodiment of a surgical mask device 10 may be seen placed adjacent a surgical patient's face.

Figure 6:
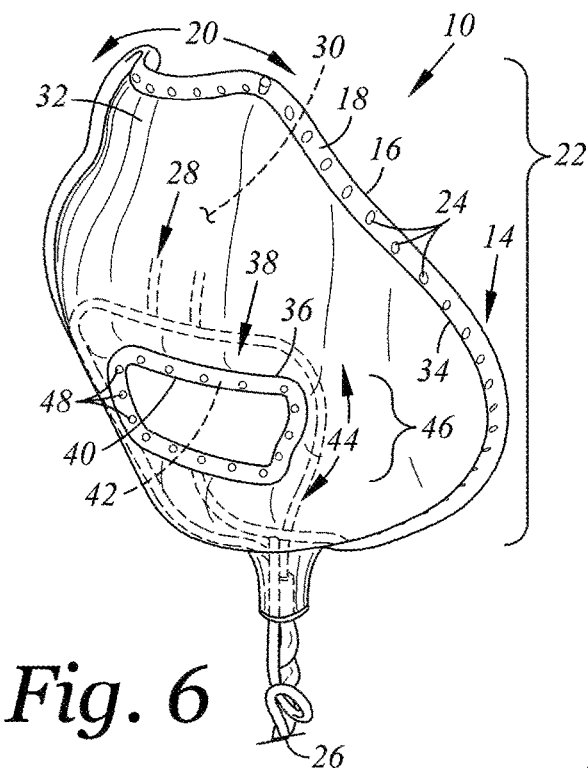
FIG. 6 is a perspective view of a surgical mask for reducing the risk of surgical fire according to another embodiment with an opening for alignment over a surgical patient's mouth.

Referring now to FIG. 6, a second exemplary embodiment of a surgical mask device 10 may be seen, in which the housing 12 has an inner perimeter 36 defining an opening sized and positioned so as to generally align with a surgical patient's mouth when the housing 12 is placed adjacent a surgical patient's face, and also including a second tubing 38, a second tubing wall 40, a second lumen 42, a second tubing length 44, a second aperture portion 46, and a plurality of second apertures 48.

The inner perimeter 36 may at least partially define an opening through the housing sized and positioned to generally align with a surgical patient's mouth when the housing 12 is placed adjacent a surgical patient's face. The inner perimeter 36 may be surrounded by the material of the housing 12 and the outer perimeter 34, as in the second exemplary embodiment, or the inner perimeter 36 and the outer perimeter 34 may be at least partially coextensive. The inner perimeter 36 may be have a generally trapezoid shape, as in the second exemplary embodiment, or may have a different shape, including but not limited to rectangular, square, oval, or ellipse. It may be preferable that the housing 12 be acutely curved or otherwise configured so that the inner perimeter 36 approaches and is contoured to the area of a surgical patient's face surrounding the patient's mouth when the housing is placed adjacent the surgical patient's face, in a similar fashion as how the outer perimeter 34 may be contoured to approach a surgical patient's face. The opening defined by the inner perimeter 36 may, in certain embodiments, allow a patient to speak substantially uninhibited. In other embodiments, the opening defined by the inner perimeter 36 may allow a surgeon to access the patient's oral cavity during surgery, such as, for example, dental or other oral surgery.

The second tubing 38 may be formed of one or more materials usable in the making of medical tubing, including but not limited to plastics, polymers, or rubbers. Preferably, the second tubing 38 is formed of a smooth, flexible material that does not cause significant discomfort when contacted with a surgical patient's face, while also being stiff enough to maintain its structural integrity and not kink or block flow of air therethrough when lightly compressed by the housing 12 being placed against a surgical patient's face. In a preferred embodiment, the second tubing 38 is formed of latex, rubber, or polyvinyl chloride. However, it any material may be utilized to form the second tubing 38 so long as that material is suitable for the intended purpose of evacuating oxygen-rich air away from a surgical patient's face. In the second exemplary embodiment, the second tubing 38 is formed to be looped unbroken adjacent to the inner perimeter 36 of the housing 12. Alternately, in other embodiments, the second tubing 38 may have breaks, branches, and terminations. The second tubing 38 may have a second tubing wall 40, a second lumen 42, a second tubing length 44, a second aperture portion 46, and a plurality of second apertures 48.

The second tubing wall 40 may at least partially define the exterior of the second tubing 38, and may at least partially circumscribe and define the second lumen 42. When not deformed, the second tubing wall 40 preferably has a generally circular cross-section, but it is contemplated herein that the second tubing wall 40 may have a differently shaped cross-section. The second tubing wall 40 preferably has a constant geometric cross-section, cross-section area, and thickness throughout the second tubing length 44, but in other embodiments the second tubing wall 40 may vary in geometric cross-section, cross-sectional area, and thickness throughout the second tubing length 44. For example, in certain embodiments it may be beneficial to utilize a second tubing wall 40 having a larger geometric cross-section, so as to better fit the face of a smaller patient and result in a more effective seal to prevent the leakage of oxygen-rich air. In other embodiments, it may be beneficial to configure the second tubing wall 40 to be more pliant and deformable at the second aperture portion 46, thereby providing a greater degree of conformity to the patient, and to be more resilient at other areas, thereby preventing kinking or occlusion which may result in ineffectiveness of the device.

The second lumen 42 may be formed within the second tubing wall 40, and may be fluidly connected to the second apertures 48 and the tubing port 26. The second lumen 42 may provide a pathway for oxygen-rich airflow to travel through so that the airflow is removed from the surgical site where it may present an elevated risk of surgical fire in the presence of electrosurgical instruments or lasers. Being formed within the second tubing wall 40, the second lumen 42 likewise has a cross-section and cross-sectional area defined by the interior of the second tubing wall 40, which in a preferred embodiment is generally circular, though in other embodiments, may take other forms, such as elliptical, oval, rectangular, square, or otherwise.

The second tubing length 44 may be the length defined by the second tubing wall 40. In the exemplary embodiment, the second tubing 38 has a second tubing length 44 that is roughly equivalent to the distance along the inner perimeter 36 of the housing 12 plus the distance from the inner perimeter 36 to the tubing port 26. In other embodiments, different configurations of the housing 12, the second tubing 38, and the tubing port 26 may result in a different second tubing length 44.

The second aperture portion 46 may be the portion of the second tubing length 44 of the second tubing wall 40 that has the plurality of second apertures 48 formed in and disposed along the second tubing wall 40. In the second exemplary embodiment, the second aperture portion 46 is the portion of the second tubing length 44 which is attached adjacent to the inner perimeter 36 of the housing 12. In other embodiments, the second aperture portion 45 may be configured differently so as to attach to the housing 12 at different areas. For example, the second aperture portion 46 may only be attached at only a portion of the outer perimeter 34 of the housing 12, may be staggered or broken up to be at multiple locations along the inner perimeter 36 of the housing 12, or may be oriented and configured differently in other configurations. The second aperture portion 46 may be attached adjacent the inner perimeter 36 of the housing 12. In the second exemplary embodiment, the second aperture portion 46 is adjacent to substantially the entire length of the inner perimeter 36, and is attached to the inner perimeter 36 so as to create an airtight seal between the material of the second tubing wall 40 and the inner perimeter 36. Alternately, in other embodiments, the second aperture portion 46 may not be adjacent to substantially the entire length of the inner perimeter 36, but instead may be attached to only a portion of the length of the inner perimeter 36, and the attachment between the inner perimeter 36 and the second tubing wall 40 may not be airtight. Such attachment may be achieved by, for example but without limitation, adhesives, fittings, fastenings, mountings, or any other ways of attaching components in medical devices together.

The plurality of second apertures 48 may be formed in and disposed along the second aperture portion 46 and be disposed in fluid communication with the second lumen 42. The second apertures 48 may also be sized and configured to be positioned proximal to the surgical patient's face so as to allow airflow to be drawn through the second apertures 48 and away from the surgical patient's face. The second apertures 48 may be, in the second exemplary embodiment, small circular holes in the second tubing wall 40 which are closely spaced together. Alternately, the second apertures 48 may be configured in other ways and to have other forms, and may be, for example but without limitation, square, oval, rectangular, elliptical, or otherwise, may be spaced closer together or further apart, and may be arranged differently. In the second exemplary embodiment, the second apertures 48 are positioned such that airflow is drawn through the second apertures 48 from both the housing patient side 30 and the housing surgeon side 32 of the housing 12 when the surgical mask device 10 is placed adjacent a surgical patient's face and connected to a suction source. However, it is contemplated that in other embodiments, the second apertures 48 may be positioned to cause airflow to be drawn in from only the housing patient side 30, or only the housing surgeon side 32 of the housing 12, or to allow selectivity in the regions from which airflow will be drawn in.

Figure 7:
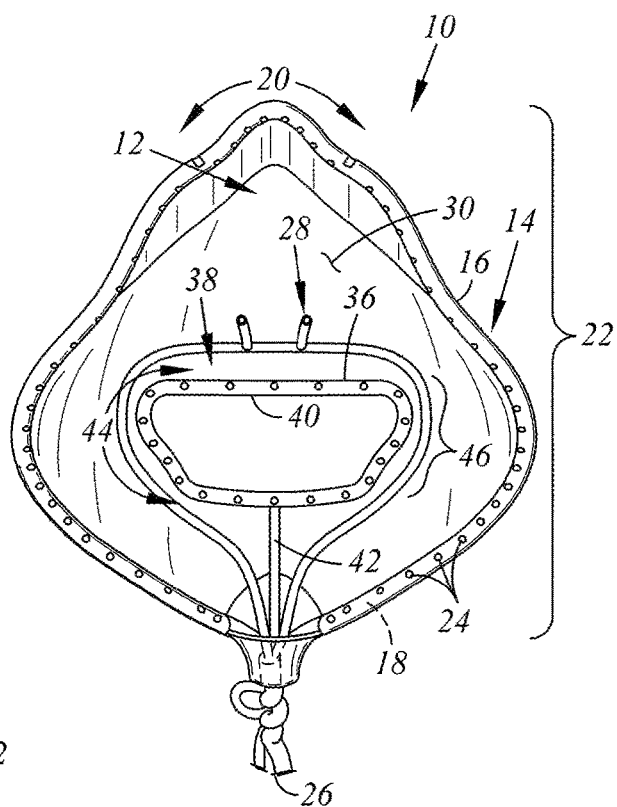
FIG. 7 is a rear view of the embodiment of FIG. 6.

Referring now to FIG. 7, a rear view from the housing patient side 30 of the second exemplary embodiment of the surgical mask device 10 may be seen. It may be seen in particular that in the second exemplary embodiment, at least some of the plurality of second apertures 48 are positioned so as to evacuate air from the patient side 30.

Figure 8:
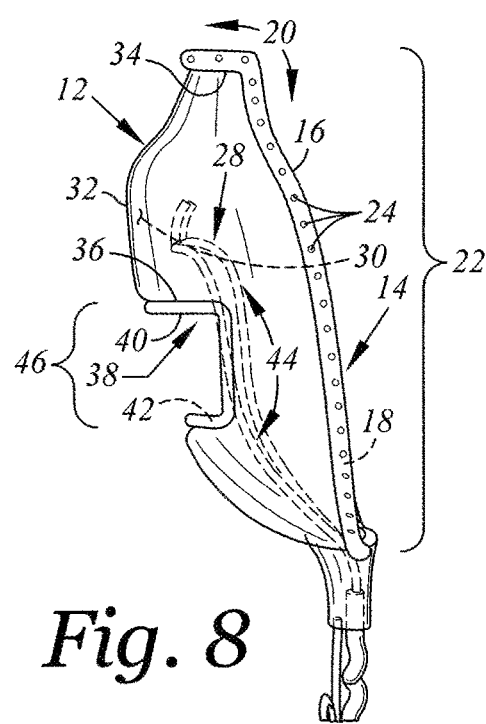
FIG. 8 is a side view of the embodiment of FIG. 6.

Referring now to FIG. 8, a side view of the second exemplary embodiment of the surgical mask device 10 may be seen.

Figure 9:
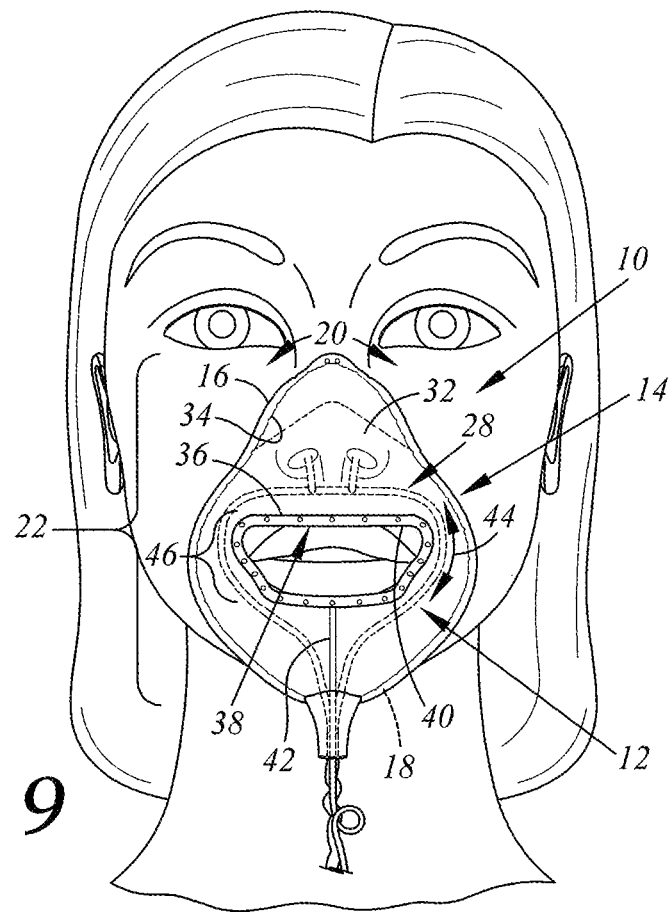
FIG. 9 is a front view of the embodiment of FIG. 6, showing placement adjacent a surgical patient's face.

Referring now to FIG. 9, a front view of the second exemplary embodiment of the surgical mask device 10 may be seen placed adjacent a surgical patient's face. It may be seen that the cannula 28 may interface with the patient's nares. Elevated oxygen concentrations resulting from leakage of supplemental oxygen from a surgical patient's nose and may be contained by the surgical mask device 10, due to the seal between the housing 12 and the surgical patient's face. As a result of the elevated oxygen concentrations being drawn into the apertures 24, 48 and subsequently through the port 26, areas of elevated oxygen concentration may not be formed at areas on the surgical patient outside of the housing 12. It may also be recognized that a patient may be allowed to speak and that a surgeon may access the oral cavity through the opening defined by the inner perimeter 36.

Figure 10:
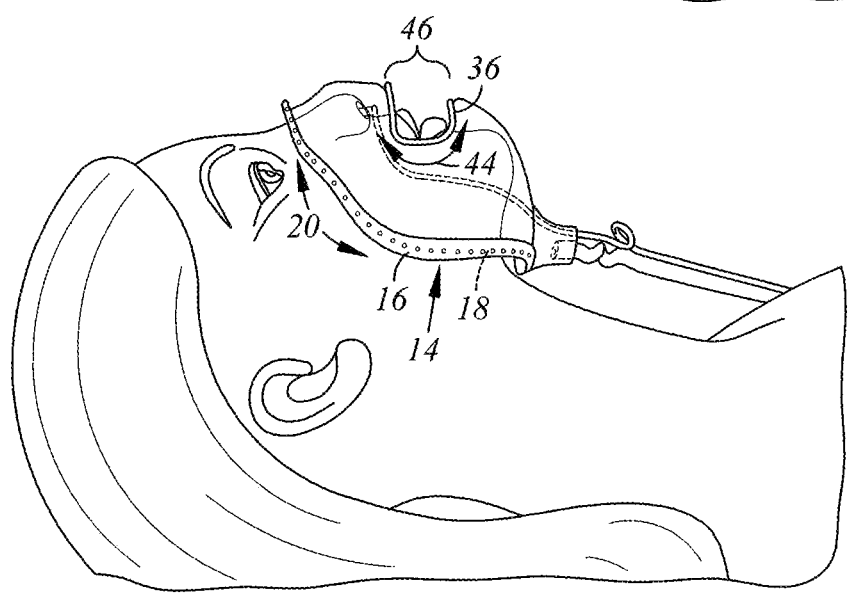
FIG. 10 is a side view of the embodiment of FIG. 6, showing placement adjacent a surgical patient's face.

Referring now to FIG. 10, a side view of the second exemplary embodiment of a surgical mask device 10 may be seen placed adjacent a surgical patient's face.

Referring now to FIG. 11, a surgical drape device 50 according to an exemplary embodiment is shown. In this exemplary embodiment, the surgical drape device 50 includes a surgical drape 52, and a tubing 54 having a tubing wall 56, a lumen 58, a tubing length 60, an aperture portion 62, a plurality of apertures 64, and a port 66.

Referring now to FIG. 12, the surgical drape 52 may be formed of any materials usable in the making of surgical drapes, including but not limited to fabrics, polymers, and plastics, or combinations thereof. In the preferred embodiment, the surgical drape 52 is formed of a laminate of a melt-blown (microfiber) layer and a spun-bond (continuous fiber) layer. The melt blown layer may be heavier and be the bottom layer, and the spun bond layer may be lighter and be the surface layer. The melt blown component may contribute to the drape's softness, opacity, absorbency and barrier abilities while the spun bond fibers may enhance the laminate's strength and integrity. An embossing or calendaring treatment may make the laminate lint-free, stronger and aesthetically pleasing. One suitable choice of material is polypropylene, for its ease of use and low cost. One goal in choosing a surgical drape material is that it be soft, comfortable, breathable, lint free, resistant to strike-through by contaminants and pathogens, and sterilizable at 250 to 280 degrees Fahrenheit by steam. The fabric material of a surgical drape may meet the permeability and biological filtration efficiency (BFE) standards. For example, a fabric for a surgical drape 52 may have a basis weight of about 40 grams per square meter, a BFE greater than 90%, a Delta P less than 5 mm, a hydrostatic head greater than 40 cm, and a grab tensile greater than 10 kg. But it should be understood that other variations or embodiments of a surgical drape 52 may also be suitable for the purposes herein.

A surgical drape 52 may comprise a fire-retardancy or anti-static additive. Suitable antistatic additives may be, for example but without limitation, long-chain aliphatic amines and amides, quaternary ammonium salts, esters of phosphoric acid, polyethelene glycol esters, polyoils, or conductive polymers or nanofibers. Suitable fire-retardancy additives may be, for example but without limitation, minerals such as alumina trihydrate and magnesium hydroxide; organohalogen compounds such as organochlorines and organobromines; and organophosphorus compounds such as triphenyl phosphate and tricresyl phosphate. It is contemplated that other additives for other purposes may be included with the surgical drape 52.

A surgical drape 52 may be compliant with the requirements of one or more of the following standards: ASTM F1670 synthetic blood penetration, AATCC 42 hydrostatic pressure, AAMI PB7O liquid barrier classification of gowns and drapes, EN 14683 BFE, synthetic blood and delta P (European protocol), EN 149:2001 inhalation resistance (European protocol), Nelson Lab SOP/ARO/006 Delta P, ASTM E 96-95 breathability, Military Specification 81705C static dissipation test, Military Specification 36954C face masks requirements, ASTM D 117 tensile tests, grab, strip, elongation, ASTM D 2859 fire retardancy, IST 80.9 alcohol repellency.

Being configured for placement adjacent a surgical patient's face means that the surgical drape 52 is configured to be able to be placed generally proximal to one or more areas of a surgical patient's face, including but not limited to the surgical patient's nose, or the surgical patient's nose and mouth. A surgical drape 52 may be adjacent a surgical patient's face by means of attachment to a surgical patient. Such attachment may be, in the exemplary embodiment, via behind-the-ear straps. In other embodiments, the surgical drape 52 may be attached or secured to the surgical patient's face in other ways, such as adhesives, tapes, straps, velcro, or other ways of attaching or securing. The surgical drape 52 may also have one or more openings therethrough. In the exemplary embodiment, the surgical drape 52 has a slit therethrough for the user's mouth, to allow for a greater ability to speak relatively unhindered and to exhale to ambient. Additionally, other openings may be present in the surgical drape. The surgical drape 52 may be shaped in any form effective to cover at least a portion of the surgical patient's lower face. In the exemplary embodiment, the surgical drape 52 is generally rectangular. Alternately, the surgical drape 52 may have any of a variety of shapes, such as oval, ellipse, square, or otherwise. The surgical drape 52 in the exemplary embodiment is generally planar before being placed over a surgical patient's face. However, it is contemplated herein that in other embodiments, the surgical drape 52 may be formed (e.g., impressed) with a general curvature or fluted or corrugated shape, or other form. The surgical drape 52 may have a drape patient side 68 which may be positioned to face the surgical patient when the surgical drape 52 is placed adjacent a surgical patient's face, and a drape surgeon side 70 which may be positioned to face away from the surgical patient when the surgical drape 52 is placed adjacent a surgical patient's face.

Referring now to FIG. 13, the tubing 54 may be formed of one or more materials usable in the making of medical tubing, including but not limited to plastics, polymers, or rubbers. Preferably, the tubing 54 is formed of a smooth, flexible material that does not cause significant discomfort when placed over a surgical patient's face, while also being stiff enough to maintain its structural integrity and not kink or block flow of air therethrough when contorted or bent. In a preferred embodiment, the tubing 54 is formed of latex, rubber, or polyvinyl chloride. However, any material may be utilized to form the tubing 54 so long as that material is suitable for the intended purpose of evacuating oxygen-rich air away from a surgical patient. In the exemplary embodiment, the tubing 54 is formed in a branched configuration with four distinct branches emanating from a central trunk, at the terminus of which is port 66. Alternately, in other embodiments, the tubing 66 may be formed with more or less branches, or may be looped or otherwise formed. The tubing 54 may have a tubing wall 56, a lumen 58, a tubing length 60, an aperture portion 62, and a plurality of first apertures 64.

The tubing wall 56 may at least partially define the exterior of the tubing 54, and may at least partially circumscribe and define the lumen 58. When not deformed, the tubing wall 56 preferably has a generally circular cross-section, but it is contemplated herein that the tubing wall 56 may have a differently shaped cross-section instead. The tubing wall 56, in the exemplary embodiment, has a constant geometric cross-section, cross-section area, and thickness throughout the aperture portion 62 of the tubing length 60, but in other embodiments the tubing wall 56 may vary in geometric cross-section, cross-sectional area, and thickness throughout the aperture portion 62 or the entirety of the tubing length 60. For example, in certain embodiments it may be beneficial to utilize a tubing wall 56 having a larger geometric cross-section at certain portions, so as vary the volume of air away from the patient's face at certain locations. In other embodiments, it may be beneficial to configure the tubing wall 56 to be more pliant and deformable at the certain locations, thereby providing a greater degree of conformity to the patient, and to be more resilient at other areas, thereby preventing kinking or occlusion which may result in ineffectiveness of the device.

The lumen 58 may be formed within the tubing wall 56, and may be fluidly connected to the apertures 54 and the port 66. The lumen 58 may provide a pathway for oxygen-rich airflow to travel through so that the airflow is removed from the surgical site where it may present an elevated risk of surgical fire in the presence of electrosurgical instruments or lasers. Being formed within the tubing wall 56, the lumen 58 likewise has a cross-section and cross-sectional area defined by the interior of the tubing wall 56, which in a preferred embodiment is generally circular, though in other embodiments, may take other forms, such as elliptical, oval, rectangular, square, or otherwise.

The tubing length 60 may be the length defined by the tubing wall 56. In the exemplary embodiment, the tubing 56 has a tubing length 60 equivalent to the length of the branches of the aperture portion 62 plus the distance of the trunk of the tubing 52 to the port 66. In other embodiments, different configurations of the tubing 54 may result in a different tubing length 60.

The aperture portion 62 may be the portion of the tubing length 60 of the tubing wall 56 that has the plurality of apertures 64 formed in and disposed along the tubing wall 56. In the exemplary embodiment, the aperture portion 62 is the portion of the tubing length 60 which is attached adjacent to and coplanar with the surgical drape 52. In certain embodiments, the aperture portion 62 may be especially configured so as to attach to the surgical drape 54 at certain areas. For example, it may be beneficial that the surgical patient's nasofacial sulcus and/or bucco-facial sulcus be specifically targeted by the aperture portion 62 as an area from which to remove airflow, due to the potential for pools of air with elevated oxygen concentration to build up in those locations as a consequence of cannulated supplemental oxygen delivery to surgical patients. As such, the exemplary embodiment positions the individual branches of the aperture portion 62 of the tubing 54 to align with each of a respective surgical patient's nasofacial and bucco-facial sulcus when the surgical drape 52 is placed adjacent the surgical patient's face. Alternately, in other embodiments, the aperture portion may be staggered or broken up to be at multiple locations along the tubing length 60 and positioned at different locations at the surgical drape 52, and may be oriented and configured differently in other configurations. The aperture portion 62 may be attached adjacent the outer perimeter of the surgical drape 52. By coplanar, it is meant that the aperture portion 62 is attached to or may be attached to the surgical drape 52 in such a fashion that the aperture portion 62 is substantially parallel to a surface of the surgical drape, and may bend or curve along with the surgical drape 52 when it is placed adjacent a surgical patient's face to match the contours of that surgical patient's face so as to not substantially deviate from being parallel with a surface of the surgical drape. Such attachment may be achieved by, for example but without limitation, adhesives, fittings, fastenings, mountings, or any other ways of attaching components in medical devices together, and it is further contemplated herein that the surgical drape 52 and the aperture portion 62 may be integrated together or contemporaneously formed, or otherwise juxtaposed.

The plurality of apertures 64 may be formed in and disposed along the aperture portion 62 and be disposed in fluid communication with the lumen 58. The apertures 64 may also be sized and configured so as to allow airflow to be drawn through the apertures 64 and away from the surgical patient. The apertures 64 may be, in the exemplary embodiment, small circular holes in the tubing wall 60 which are closely spaced together. In other embodiments, the apertures 64 may be configured in other ways and to have other forms, and may be, for example but without limitation, square, oval, rectangular, elliptical, or otherwise, may be spaced closer together or further apart, and may be arranged differently. In the exemplary embodiment, the apertures 64 are positioned such that airflow is drawn through the apertures 64 from drape surgeon side 70 when the surgical drape device 50 is placed adjacent a surgical patient's face and connected to a suction source. It is further contemplated that in other embodiments, the apertures 54 may be positioned to cause airflow to be drawn in from only the drape patient side 68, or only the drape surgeon side 70, or from both the drape patient side 68 and the drape surgeon side 70 selectively or simultaneously.

The surgical mask port 66 may be any port which is in fluid connection with the lumen 58 and allows fluid connection to a suction source and the passage therethrough of airflow. The surgical mask port 66 may engage with an external suction source in any way which produces a sufficient seal to result in suction at the apertures 64 to result in evacuation of airflow. Such engagement may be, for example but without limitation, threaded, frictional, or coupling engagement. In the exemplary embodiment, the surgical mask port 66 is the terminal end of the tubing 54 which may fit over or be placed within a frictionally engaging seal, such as a nozzle head or a larger tube which may be secured with a tube or hose clamp. Alternately, in other embodiments, the surgical mask port 66 may be more elaborate, and may be, for example, a locking system configured to allow for more specific fluid connection to a particular suction source. The surgical mask port 66 may also have control elements for initiating or regulating the flow therethrough of evacuated airflow, for controlling the suction power of the suction source remotely, or other control elements for modulating functionality of the surgical mask device 10. For example, it may seen that in the exemplary embodiment, a valve is positioned proximal to the surgical mask port 66 for regulating and controlling the airflow through the lumen 58.

Figure 14:
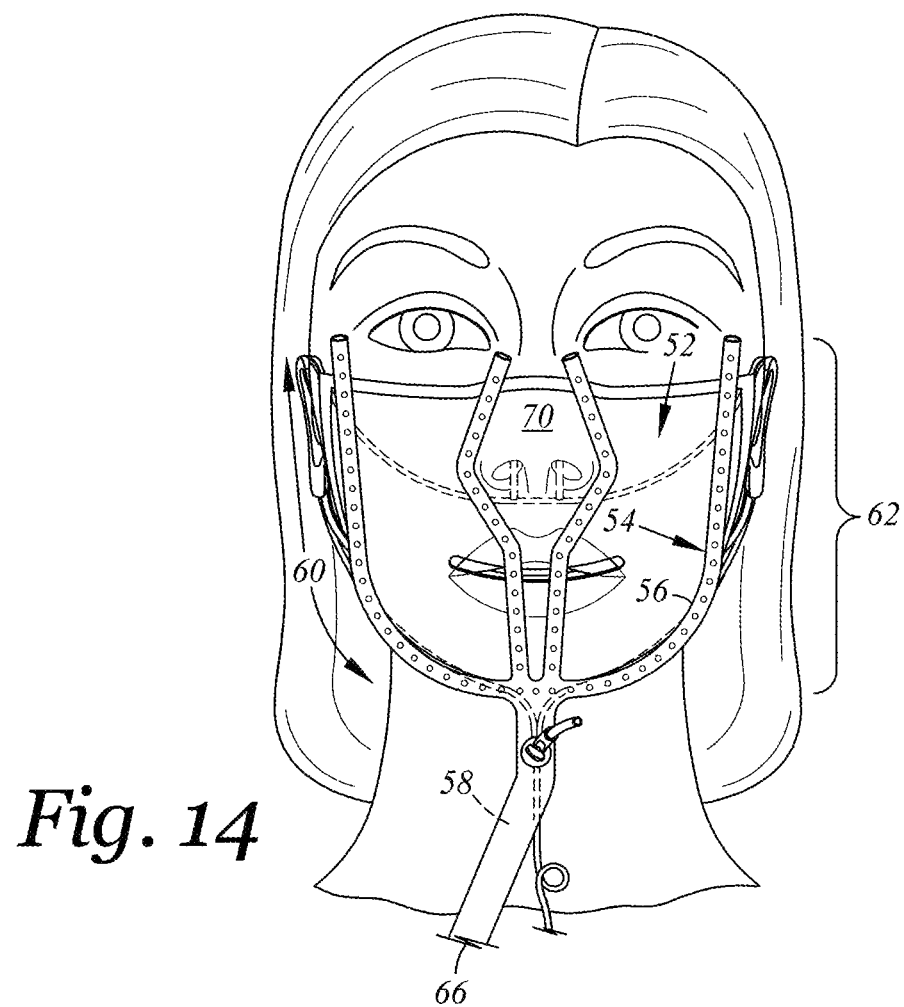
FIG. 14 is a front view of the embodiment of FIG. 11, showing placement adjacent a surgical patient's face.

Referring now to FIG. 14, a front view of the exemplary embodiment of FIG. 11 is shown placed adjacent the nose and mouth of a surgical patient. It may be seen how the branches of the aperture portion 62 are sized and configured with the surgical drape to align over the surgical patient's nasofacial sulcus and bucco-facial sulcus.

Figure 15:
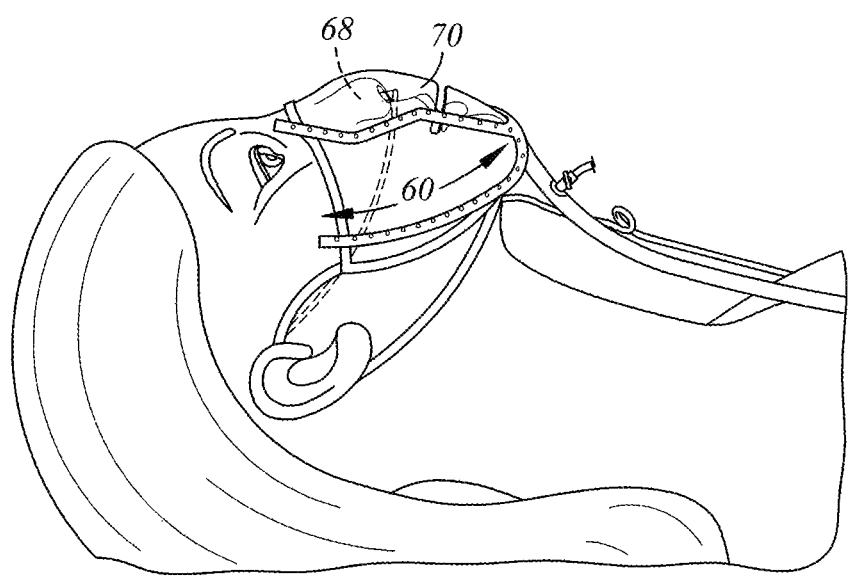
FIG. 15 is a side view of the embodiment of FIG. 11, showing placement adjacent a surgical patient's face.

Referring now to FIG. 15, a side view of the exemplary embodiment of FIG. 11 is shown placed adjacent the nose and mouth of a surgical patient.

Figure 16:
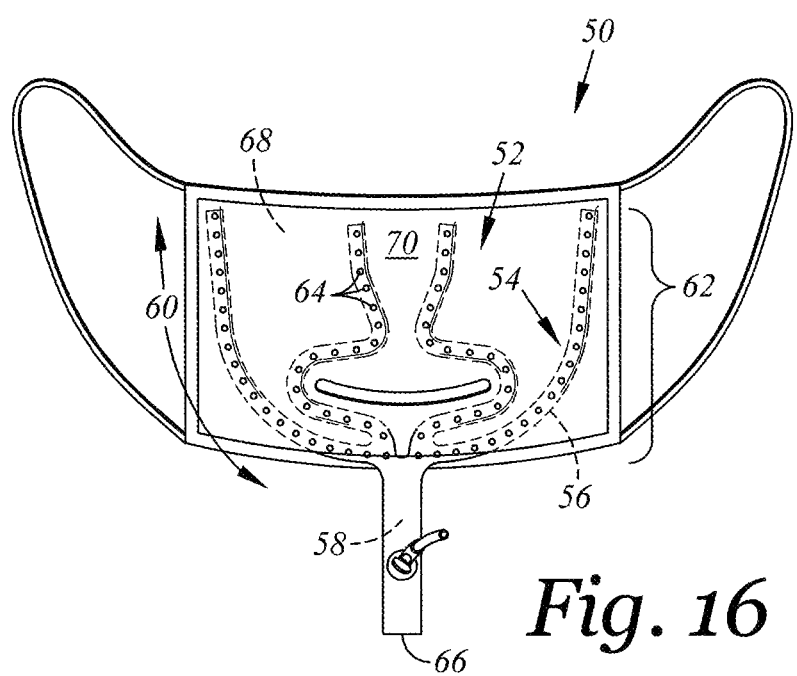
FIG. 16 is a front view of a surgical mask for reducing the risk of surgical fire according to a further embodiment with the tubing integrated with the surgical drape.

Referring now to FIG. 16, a second exemplary embodiment of a surgical drape device 50 is shown. In this embodiment, at least a portion of the aperture portion 62 of the tubing 54 is integrated with the material of the surgical drape 52. It may be seen that in this second exemplary embodiment, the tubing wall 56 may be formed to be contiguous with the surgical drape, such that the material of the surgical drape 52 itself is juxtaposed with the material of the tubing wall 56. It may be seen that in such an embodiment, the lumen 58 may be defined by the material of the surgical drape 52 as well.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A surgical mask for reducing risk of surgical fire near a surgical patient's face during use of supplemental oxygen, the surgical mask comprising:
   a housing for placement adjacent the surgical patient's face, the housing having a radially inward patient side; a radially outward surgeon side; a longitudinal axis; an outer perimeter around the housing; and an opening unobstructed by tubing and extending therethrough from the surgeon side to the patient side, the unobstructed opening defining an inner perimeter and being disposed along the longitudinal axis of the housing;
   wherein, when the surgical mask is placed adjacent the surgical patient's face, the housing defines a cavity between the patient side and the surgical patient's face, the outer perimeter sealingly contours to the surgical patient's face, the longitudinal axis aligns with the surgical patient's nose, and the unobstructed opening aligns with the surgical patient's mouth;
   a first tubing positioned around the inner perimeter, the first tubing comprising:
      a first tubing wall defining an internal lumen, the first tubing wall having a first length and being adjacently attached to the inner perimeter;
      a plurality of first apertures formed through the first tubing wall and spaced in intervals along the first length of the first tubing wall, each of the plurality of first apertures being disposed in fluid communication with the internal lumen and being sized and configured to be positioned proximal to the surgical patient's mouth, such that airflow from within the cavity from the use of supplemental oxygen is drawn away from the surgical patient's face and through one or more of the plurality of first apertures and through the internal lumen, when the first tubing is placed in fluid communication with a suction source; and
   a cannula positioned under the housing and within the cavity for delivering supplemental oxygen to the surgical patient's nose, the cannula comprising a cannula tube that surrounds the first tubing.

2. The surgical mask of claim 1, further comprising:
   a second tubing positioned around the outer perimeter, the second tubing comprising:
      a second tubing wall defining an internal lumen, the second tubing wall having a second length and being attached adjacently to the outer perimeter; and
      a plurality of second apertures formed through the second tubing wall and spaced in intervals along the second length of the second tubing wall, each of the plurality of second apertures being disposed in fluid communication with the internal lumen of the second tubing wall and being sized and configured to be positioned proximal to the surgical patient's face, such that airflow from within the cavity from the use of supplemental oxygen is drawn away from the surgical patient's face and through one or more of the plurality of second apertures and through the internal lumen of the second tubing wall, when the second tubing is placed in fluid communication with the suction source.

3. The surgical mask of claim 2, wherein the second tubing wall has a cylindrical shape; and wherein the second tubing length is attached along substantially an entirety of the outer perimeter of the housing.

4. The surgical mask of claim 2, further comprising a port sized and configured to be disposed in fluid communication with the suction source, the port being disposed along the longitudinal axis; and wherein the first tubing is fluidly coupled to the port via a first tubing extension extending from the first length of the first tubing wall.

\* \* \* \* \*